United States Patent
Rehm

(10) Patent No.: US 11,160,765 B2
(45) Date of Patent: Nov. 2, 2021

(54) COMPOSITIONS AND METHODS OF TREATING FUNGAL INFECTIONS OF THE NAILS

(71) Applicant: KBR Incorporated, Carlsbad, CA (US)

(72) Inventor: Kenneth Rehm, Carlsbad, CA (US)

(73) Assignee: KBR Incorporated, Carlsbad, CA (US)

( * ) Notice: Subject to any disclaimer, the term of this patent is extended or adjusted under 35 U.S.C. 154(b) by 6 days.

(21) Appl. No.: 16/897,917

(22) Filed: Jun. 10, 2020

(65) Prior Publication Data

US 2020/0375916 A1 Dec. 3, 2020

Related U.S. Application Data

(63) Continuation-in-part of application No. 16/247,953, filed on Jan. 15, 2019, now abandoned.

(60) Provisional application No. 62/618,175, filed on Jan. 17, 2018.

(51) Int. Cl.

| A61K 9/70 | (2006.01) |
|---|---|
| A61K 8/67 | (2006.01) |
| A61K 47/18 | (2017.01) |
| A61K 31/045 | (2006.01) |
| A61P 31/10 | (2006.01) |
| A61K 47/46 | (2006.01) |
| A61K 47/22 | (2006.01) |
| A61Q 19/00 | (2006.01) |
| A61K 8/9789 | (2017.01) |
| A61K 8/9794 | (2017.01) |
| A61K 8/98 | (2006.01) |
| A61K 8/42 | (2006.01) |
| A61K 31/325 | (2006.01) |

(52) U.S. Cl.
CPC ............ *A61K 9/7084* (2013.01); *A61K 8/42* (2013.01); *A61K 8/671* (2013.01); *A61K 8/675* (2013.01); *A61K 8/676* (2013.01); *A61K 8/678* (2013.01); *A61K 8/9789* (2017.08); *A61K 8/9794* (2017.08); *A61K 8/981* (2013.01); *A61K 31/045* (2013.01); *A61K 31/325* (2013.01); *A61K 47/18* (2013.01); *A61K 47/22* (2013.01); *A61K 47/46* (2013.01); *A61P 31/10* (2018.01); *A61Q 19/00* (2013.01)

(58) Field of Classification Search
CPC ....... A61P 31/10; A61Q 19/00; A61K 9/7084; A61K 8/678; A61K 47/18; A61K 31/045; A61K 47/16; A61K 47/22; A61K 8/9789; A61K 8/9794; A61K 8/981; A61K 8/42; A61K 8/675; A61K 8/671; A61K 31/325
See application file for complete search history.

(56) References Cited

U.S. PATENT DOCUMENTS

| 6,043,407 A * | 3/2000 | Lodhi ................ A61L 15/38 602/48 |
|---|---|---|
| 6,217,887 B1 | 4/2001 | Beerse et al. |
| 6,254,897 B1 | 7/2001 | Shao |
| 2006/0141014 A1 * | 6/2006 | Eknoian ............ A45D 40/00 424/443 |
| 2011/0008474 A1 | 1/2011 | Boegli |

OTHER PUBLICATIONS

Sudaxshina Murdan, Enhancing the Nail Permeability of Topically Applied Drugs, 5 Exp. Opin. Drug Del. 1267, 1274-76 (Year: 2008).*

Aditya K. Gupta, Maryse Paquet, Improved Efficacy in Onchomycosis Therapy, 31 Clinics Dermatol. 555, 558-60 (Year: 2013).*

* cited by examiner

*Primary Examiner* — Sean M Basquill
(74) *Attorney, Agent, or Firm* — Veros Legal Solutions LLP

(57) ABSTRACT

Compositions and methods for reducing the symptoms of skin conditions associated with the nail and surrounding tissue are provided. A medicated pad for cleaning and treating the nail and surrounding tissue is described, wherein said pad is saturated with a therapeutic composition comprising certain botanicals, an antimicrobial agent, a surfactant, and a moisturizing agent. The skin and nail conditions can include fungal infections of the nails. Kits for treating fungal infections of the nails are likewise described. Optionally, the kit may include a hydrating composition which includes shea butter, aloe, vitamins, arnica, emu oil, urea, and Vitamins C, A, E, and D. A bandage comprising a therapeutic pad instilled with an antifungal agent is also provided.

7 Claims, 3 Drawing Sheets

COMPOSITIONS AND METHODS OF TREATING FUNGAL INFECTIONS OF THE NAILS

CROSS REFERENCE TO RELATED APPLICATION

This application is a continuation-in-part of co-pending U.S. patent application Ser. No. 16/247,953, filed on Jan. 15, 2019 and claiming the benefit of U.S. Provisional Application No. 62/618,175, filed on Jan. 17, 2018, the contents of which are hereby incorporated in their entirety.

BACKGROUND OF THE INVENTION

Field of the Invention

Embodiments of the invention relate to compositions for treating conditions of the nail and surrounding skin. More particularly, the invention includes compositions and methods for ameliorating the signs and symptoms associated with infections of the nails. Also disclosed are methods of treating the signs and symptoms of fungal infections. Kits comprising an anti-fungal therapeutic as well as bandages comprising an anti-fungal therapeutic are likewise provided.

Description of the Related Technology

Fungal infection of the nail, also known as onchomycosis or tinea unguium, is a relatively common condition that up to ten percent of all adults in Western countries experience. The percentage of individuals infected with a nail fungus can increase to 20% of adults who are 60 years or older.

Nail fungal infections can be caused by a dermatophyte fungus such as *Trichophyton rubrum*. Yeasts and molds can also be responsible for fungal infections of the nail. In healthy individuals, a fungal infection of the nails can be transmitted by exposure to moist, wet areas such as communal showers or from nail salons, where instruments are inadequately sanitized. Elderly people as well as people with underlying disease states such as AIDS, diabetes, cancer, psoriasis, or someone taking immunosuppressive medications such as steroids are also at a higher risk of experiencing a fungal infection of the nail.

Typically, fungal infections of the nail can begin as a white or yellow spot on or under the tip of a fingernail or toenail and as the infection progresses, can result in the discoloration, thickening, and deterioration of the nail. Signs of a fungal nail infection can also include a brittle, crumbly or ragged appearance of the nail, a nail which is distorted in shape, as well as a nail bed that is dull. In some cases, the nail can appear dark in color, which is caused by debris building gup under the nail. In other instances, the nail can become loose or lift up as a result of a fungal infection.

While nail infections can pose cosmetic concerns, they are also responsible for causing pain and discomfort due to the changes of the nail. Treatment for fungal nails includes keeping the nail trimmed and filed to reduce the amount of fungus in the nail. Oral antifungal therapy including the use of griseofulvin, tervinafine, itraconazole, or fluconazole has been prescribed to treat fungal nail infections. However, many of the oral therapies only works between about 50-75% of the time and, like many medications, come with unwanted side effects. Even when oral therapy does work, the fungus may come back in about 20-50% of the time. Other treatment protocols include the use of laser therapy or photodynamic therapy, use of electrical current to help absorption of topical antifungal medications, as well as the use of a nail lacquer that alter the microclimate of the nail to make it more difficult for a fungus to grow. Topical medications and creams have likewise been used to treat fungal nail infections but are generally thought to be less effective than oral medications due at least in part to the difficulty in penetrating the hard exterior of the nail. Topical treatments may require daily application for a period of time up to one year in order to see results. These topical treatments include both prescription topical medications such as ciclopirox, efinaconazole, and tavaborole as well as non-prescription treatments such as undecylenic acid and/or propylene glycol, vinegar, and Vicks VapoRub.

Curing fungal nails can be challenging and treatment can take as long as 18 months. Moreover, relapse and reinfection are quite common (40-70% reinfection rate). There remains a need for effective treatments for fungal nail infections which treat the infection without the side effects of an oral medication.

SUMMARY

Compositions, kits, and methods are described for reducing the symptoms of fungal nail contamination are provided. In one aspect, a medicated pad for use in ameliorating symptoms of conditions of the skin and nail is described. The medicated pad may include a nonwoven disc having a first surface and a second surface; wherein at least one of the first or second surfaces is textured. The medicated pad may further include an aqueous therapeutic composition. The composition can include an effective amount of an antimicrobial agent; an effective amount of a surfactant; a moisturizing agent; and an effective amount of a botanical agent. Advantageously, the nonwoven disc is saturated with the therapeutic composition.

In one aspect, the medicated disc is incorporated into an adhesive nail bandage such that the medicated disc or therapy pad can be placed directly on a nail to be treated. The bandage comprising a therapy pad can be contacted with a nail surface for 24 hours or longer. The therapy pad can be pretreated with an anti-fungal composition. Alternatively, the therapeutic agents can be administered specifically to therapy pad by the user prior to application and adherence to the nail surface. In still another aspect, the bandage may include spider web fibers to promote healing.

In some aspects, the medicated pad is moistened with antimicrobial agent such as an antifungal agent, an antibacterial agent, or an antiviral agent. The antifungal agent may be tolnaftate. Optionally, the therapeutic composition includes a surfactant such as decyl glucoside or non-ionic polyglucoside.

In another aspect, the medicated pad may include a moisturizer such as allantoin, urea, glycerol triester, or combinations thereof.

The medicated pad advantageously includes a botanical agent such as extract of calendula, chamomile, cornflower, linden leaf, St. Johns wart, garlic, oregano oil, tea tree oil, lavender oil, clove oil, cinnamon oil, and combinations thereof. Optionally, the therapeutic composition may include an effective amount of a disinfectant such as isopropyl alcohol.

In yet another aspect, a system for treating conditions of the skin and nail, are provided. The system may include a container housing a medicated pad having a textured surface; and an aqueous solution of a therapeutic composition. The therapeutic composition may include an effective amount of an antimicrobial agent; an effective amount of a surfactant; a moisturizing agent; and an effective amount of a botanical agent. Advantageously, the system further includes instructions for applying the medicated pad to the surface of a nail bed and surrounding skin to clean the nail bed and surrounding skin surfaces. The botanical agent may include extract of calendula, chamomile, cornflower, linden leaf, St. Johns wart, garlic, oregano oil, clove oil, cinnamon oil, tea tree oil, lavender oil, or combinations thereof Optionally, the system can include a second container, which houses a hydrating composition as well as instructions for applying the hydrating agent to the treated surface including the nail bed and surrounding skin after cleaning the nail bed and surrounding skin. The hydrating composition can be massaged into the skin. Advantageously, the hydrating composition includes an effective amount of shea butter; an effective amount of aloe vera powder; an effective amount of arnica; an effective amount of vitamins such as vitamin C, vitamin A, vitamin E, Vitamin B3, Vitamin D and combinations thereof; an effective amount of emu oil; and an effective amount of urea.

In still another aspect, a method of treating a nail infection is provided. The method may include providing a saturated medicated pad having at least one textured surface; wherein the pad is saturated with a therapeutic solution. The therapeutic solution can include an effective amount of an antimicrobial agent; an effective amount of a surfactant; a moisturizing agent; and an effective amount of a botanical agent.

Treatment may further include applying the textured surface of said medicated pad to the surface of a nail and surrounding tissue to clean and debride the surface.

Optionally, the method may include administering a hydrating agent to the surface of the nail and surrounding tissue after cleaning with the medicated pad. The hydrating agent can include an effective amount of shea butter; an effective amount of aloe vera powder; an effective amount of arnica; an effective amount of vitamins such as vitamin C, vitamin A, vitamin E, Vitamin B3, Vitamin D and combinations thereof; an effective amount of emu oil; and an effective amount of urea.

In another aspect, a method of treating a condition of the skin and nails is disclosed. The method may include identifying an individual in need thereof; and applying a medicated pad to the surface of the skin and nails of the individual. The condition may include a bacterial infection, a viral infection, psoriasis, inflammation, pain, and eczematous dermatitis, and combinations thereof.

DETAILED DESCRIPTION

Figure 1:
FIG. 1 is a photograph of the left and right foot of an individual presenting with a fungal infection of the toenails.

After reading this description, it will become apparent to one skilled in the art how to implement the invention in various alternative embodiments and alternative applications. However, all the various embodiments of the present invention will not be described herein. It is understood that the embodiments presented here are presented by way of an example only, and not limitation. As such, this detailed description of various alternative embodiments should not be construed to limit the scope or breadth of the invention as set forth below.

Embodiments of this application relate to compositions for treating infections of the nail. Also disclosed are medicated pads for treating disorders of the nail. In certain embodiments, compositions, methods and systems for treating fungal infections of the nails are disclosed. Additionally, systems and kits for the treatment of nail infections comprising a plurality of medicated pads and optionally, a moisturizer are provided. Methods of treating fungal infections of the nail with antifungal and/or antibacterial agents are likewise described.

The invention is based, in part, on the surprising discovery of synergistic benefits of a topical therapeutic composition coupled with a nail cleansing pad. This unique combination of therapeutic composition and medicated pad provide both kerolytic properties as well as penetrating properties to reduce the symptoms of nail infections. Thus, in one embodiment, a nail cleansing pad is provided. As will be described below with reference to FIGS. 3-5, the medicated pad can be a therapy pad adhered or otherwise in communication with an adhesive bandage. The nail cleansing pads are designed to clean the surface of the nail by debriding skin and fungal and/or bacterial contaminates while the therapeutic composition conditions and penetrates the surface of a nail including the nail, cuticles, and surrounding skin. The combination of the medicated cleansing pad and therapeutic composition serve to decrease damaging inflammation of the skin and treating the underlying infection while soothing, hydrating, and cleaning the skin and nail plate of microbes such as fungus, bacteria, and viruses. Notably, this cleaning is accomplished without harming the protective acid mantle layer of the skin. The medicated pads serve to generate a healthy pH and aid in the removal of hard dead skin while increasing the skin's permeability to the therapeutic composition.

The invention can include a system for treating nail infections comprising a container and a plurality of cleansing and debriding pads which are saturated with an active therapeutic composition hereinafter described. As used herein, saturated is meant to include wetted, impregnated, moistened, or any other similar term to convey that the pad is exposed to the therapeutic composition in such a way as to absorb at least a portion of the therapeutic composition on the pad surface such that a previously dry pad is made moist to become a medicated pad. The plurality of pads are configured to be stacked inside the container with a therapeutic composition which impregnates into the pads by capillary action. The pad is advantageously highly absorbent, non-linting, disposable, and debriding. It may be constructed of either woven or nonwoven material. In a preferred embodiment, the pad is constructed of a nonwoven material such as a nonwoven cotton. The pad may be inserted in the container through the open end and a therapeutic composition is introduced into the container so that it is absorbed by the pad. The open sided container may further include a sealing layer (not shown) to seal the saturated pads with the therapeutic composition and to prevent drying.

The nail cleansing pads of the present invention are configured to be impregnated with the therapeutic composition and absorb at least a portion of the therapeutic composition. Additionally, the pads provide surface for scrubbing the nail and surrounding tissue of an individual. Preferably, the pads comprise a nonwoven material fused together to form a multiple layer medicated pad. Pads of the present invention can have a plurality of textural differences such as smooth nonwoven material fused to a coarse nonwoven material to create varying degrees of textural differences. In one embodiment, the cleansing pad is disc shaped. However, it will be appreciated by a person of skill in the art that the pad can be in square, rectangular, or any other suitable shape.

Although not limited thereto, in some aspects, the present invention includes nonwoven fabrics derived from "oriented" or carded fibrous webs composed of textile-length fibers, the major proportion of which are oriented predominantly in one direction. Exemplary of such fibers are the natural fibers such as cotton and wool and the synthetic or man-made cellulosic fibers, notably rayon or regenerated cellulose, such as those supplied by BASF.

Other fibers of a synthetic or man-made origin may be used such as: polyamide fibers such as nylon 6, nylon 66, nylon 610, etc.; polyester fibers such as "Dacron", "Fortrel" and "Kodel"; acrylic fibers such as "Acrilan", "Orlon" and "Creslan"; modacrylic fibers derived from polyethylene and polypropylene; cellulose ester fibers such as "Arnel" and "Acele"; polyvinyl alcohol fibers, etc.

Methods of making nonwoven cloths are not a part of this invention and, being well known in the art, are not described in detail herein. Generally, however, such cloths are made by air- or water-laying processes in which the fibers or filaments are first cut to desired lengths from long strands, passed into a water or air stream, and then deposited onto a screen through which the fiber-laden air or water is passed. The deposited fibers or filaments are then adhesively bonded together, using the resins of the present invention, dried, cured, and otherwise treated as desired to form the nonwoven cloth.

The preferred nonwoven cloth substrates used in the invention herein are generally adhesively bonded fibers or filamentous products having a web or carded fiber structure (when the fiber strength is suitable to allow carding) or comprising fibrous mats in which the fibers or filaments are distributed haphazardly or in random array (i.e., an array of fibers in a carded web where partial orientation of the fibers is frequently present, as well as a completely haphazard distributional orientation), or substantially aligned. The fibers or filaments can be natural (e.g., wool, silk, jute, hemp, cotton, linen, sisal, or ramie) or synthetic (e.g., rayon, cellulose ester, polyvinyl derivatives, polyolethins, polyamides, or polyesters) as have been described hereinabove.

The absorbent properties preferred herein are particularly easy to obtain with nonwoven cloths and are provided merely by building up the thickness of the cloth, i.e., by superimposing a plurality of carded webs or mats to a thickness adequate to obtain the necessary absorbent properties, or by allowing a sufficient thickness of the fibers to deposit on the screen. Any denier of the fiber (generally up to about 15 denier) can be used, inasmuch as it is the free space between each fiber that makes the thickness of the cloth directly related to the absorbent capacity of the cloth. Thus, any thickness necessary to obtain the required absorbent capacity can be used.

The cleansing pads are combined with a therapeutic composition, which is in solution, such that the cleansing pads are moistened, impregnated, or otherwise saturated with the therapeutic composition as will be described in greater detail below. The therapeutic composition is advantageously in aqueous solution and is readily absorbed by the pads such that the pads are moistened. In some embodiments, the therapeutic composition is formulated as an oil and is likewise readily absorbed by the pads such that the pads are moistened.

The cleansing pads can be used as a cleansing cloth to wipe away dirt, oils, and odor-causing bacteria and fungus from the surface of the skin in an individual in need thereof. Additionally, when used to clean the nail surface and surrounding surfaces, the pad aids in making the skin and cuticles softer as well as helping to loosen debris for more effective nail management. Moreover, the textured surface of the pad is adapted to soothe and gently clean contaminants that thrive in between dry, cracked, scaly skin and in between the toes. In other embodiments, the pad is adapted to clean the surface of the nail and to soften the nails, which facilitates easy and safer nail trimming.

The active therapeutic composition for which the cleansing pads are saturated is advantageously formulated in an aqueous solution. In another embodiment, the composition is formulated in an oil solution. The composition is formulated to clean and moisturize the nail surface as well as the surrounding tissue, treat microbes such as fungus, bacteria and viruses, and lower the pH of the treated surface from a pH of 7 to a pH of around 6.5, 6.0, 5.5, or 5. The reduction in pH promotes the delivery of antimicrobial agents, moisturizers, fragrance, botanicals, or combinations thereof into the skin. In some aspects, the composition comprises an effective amount of citric acid to reduce the pH to around 5.5.

In one embodiment, the therapeutic composition comprises about 75% purified water. In some embodiments, the composition comprises greater than 76%, 77%, 78%, 79%, 80%, 81%, 82%, 83%, 84%, 85%, 86%, 87%, 88%, 89%, or 90% purified water. In one embodiment, the therapeutic composition comprises about 85% purified water. The therapeutic composition can further include a surfactant, preferably a mild non-ionic alky polyglucoside surfactant such as capryl glucoside, coco glucoside, lauryl glucoside, decyl glycoside or combinations thereof in an amount of between about 5 to 20% of the formulation. In one embodiment, the surfactant is decyl glucoside in an amount of around 10% w/w of the formulation.

The therapeutic composition also includes an antimicrobial agent to remove fungus, bacteria and/or viruses from the surface of a nail. The antimicrobial agent can include a topical antibiotic selected from the group consisting of sulfacetamide sodium, bacitracin/polymyxin B, erythromycin, silver sulfadiazine, neomycin, retapmulin, mupirocin, mafenide, tolnaftate, clotrimazole, econazole nitrate, miconazole, terbinafine, fluconazole, ketoconazole, amphotericin, benzoic acid, undecyclenic acid, nystatin, naftifine, ciclopirox, efinaconazole, terbinafine, tavaborole, penciclovir, acyclovir, and combinations thereof. The antimicrobial agent is present in an amount of between about 0.1 and 5% w/w of the composition. In one embodiment, the antimicrobial agent is tolnaftate in an amount of about 1.0% w/w of the composition. The antimicrobial agent can be a botanical agent such as oregano oil, clove oil, cinnamon oil, tea tree oil or combinations thereof, which possess antibacterial, antiviral, and antifungal properties. The clove oil may be in the amount of about 10% w/w of the formulation. In some embodiments, the therapeutic composition comprises about 1% w/w of oregano oil to treat foot or nail fungus. In another embodiment, the therapeutic composition comprises an effective amount of an antimicrobial agent such as tolnaftate and a natural antimicrobial agent selected from the group consisting of oregano oil, clove oil, tea tree oil, cinnamon oil, or combinations thereof.

The therapeutic composition further includes a moisturizing agent. In one embodiment, the moisturizing agent is allantoin, urea, or combinations thereof. Allantoin helps skin to lock in moisture and encourages skin to shed dead cells as well as grow new ones, which promotes healthy cell development and prevents dull, sallow skin. It can soften the horny substance (keratin) that holds the top layer of skin cells together, which helps the dead skin cells fall off, helps the skin to keep in more water, and leaves the skin feeling smoother and softer. Allantoin conditions, moisturizes, protects, soothes, and promotes healing. In one embodiment, allantoin is present in the composition in an amount of between about 0.05 to about 5% w/w of the composition. In another embodiment, the composition comprises about 0.1% w/w allantoin. Urea is a humectant which helps the skin maintain a healthy moisture balance, keeping it soft, supple, youthful, and bringing relief to a dry skin. Urea reduces roughness on a skin surface by maintaining skin hydration. When urea is applied to the skin, it penetrates the stratum corneum, where it readily absorbs and retains water, thus increasing the capacity of the skin to hold moisture and rehydrate. In addition to improving skin moisture, urea is associated as having anti-itch properties and provide a natural exfoliant. Urea has been shown to increase the skin permeability of certain skin care ingredients, working as a vehicle for other performance ingredients, encouraging them to penetrate the epidermis easily. Urea can be present in the composition in an amount of between about 0.05-1.0% w/w. In some embodiments, the composition comprises about 0.1% w/w urea. In another embodiment, the moisturizing agent is an effective amount of glycerol triester.

In some embodiments, the therapeutic composition includes an effective amount of a preservative. Advantageously, the preservative is paraben-free and formaldehyde-free. The preservative can include phenoxyethanol, caprylyl glycol, and combinations thereof. In one embodiment, the preservative is optiphen. The preservative is present in an amount between about 0.1 to 1.0% w/w of the composition. In another aspect, the composition comprises about 0.75% w/w optiphen.

The composition can further include an effective amount of a disinfectant. The disinfectant can be an alcohol such as isopropyl alcohol or a botanical agent having disinfecting properties. Suitable botanical agents include, without limitation, lemongrass, citrus, lavender, bergamot, tea tree oil, essential oils, grapefruit extract, rosemary, cinnamon, eucalyptus, lemon, and/or clove. The botanical agents can include between about 1-10% w/w of lavender, eucalyptus, oregano, lemongrass, or cinnamon oil or combinations thereof. In a preferred embodiment, the formulation comprises about 5.0% w/w of the formulation. In still another embodiment, the disinfectant can be white distilled vinegar. The disinfectant can be present in an amount of between 0.1 to 2.0% w/w of the composition. In one embodiment, the disinfectant is isopropyl alcohol and is present in the amount of about 0.5% w/w of the composition.

The therapeutic composition for use in treating nail infections can further include an effective amount of an essential oil such as tea tree oil (Malaleuca alternifolia), lavender oil (*Lavandula angustifolia*), or combinations thereof. An effective amount of tea tree oil and lavender oil is generally between about 0.1 to about 1% w/w, more preferably between about 0.25% to about 0.5% w/w of the composition. Tea tree oil may be applied to the skin for its natural anti-inflammatory and antiseptic properties. Moreover, tea tree oil is associated with the treatment of infections such as fungal infections of the nail, lice, scabies, athlete's foot, and ringworm. It is believed to be effective at least in part because it helps to remove dry and dead skin cells including psoriatic plaques in individuals suffering from psoriasis. It also possesses antibacterial, antimicrobial, antiviral, antifungal, antiseptic, and anti-inflammatory properties which work to relieve itching, redness, and burning. Moreover, it is believed to control the overproduction of skin cells. Lavender oil also benefits the skin due to its antimicrobial and antioxidant characteristics, bringing rapid healing to dry skin as well as cuts and scrapes.

In yet another aspect, the therapeutic composition can comprise an effective amount of one of a plurality of botanical agents which include, without limitation: extracts of calendula, chamomile, cornflower, linden leaf, St. John's wart, garlic, and coneflower. Briefly, extract of calendula possesses antiviral activity as well as serves as an anti-inflammatory for the skin. Linoleic acid which is found in high concentrations of calendula is a powerful anti-inflammatory agent. Calendula-based gels and topical ointments help to speed recovery and healing, improve skin firmness, promote hydration, increase blood flow and oxygen to infected areas, and act as an anti-fungal, astringent, and healing promoter. Chamomile possesses many powerful skin properties such as anti-inflammatory, anti-fungal, antibacterial, antiseptic, and contains essential oils and antioxidants. Additionally, it is hypoallergenic and helps to reduce skin irritants by neutralizing free radicals. Similarly, cornflower has anti-inflammatory properties and promotes wound healing. It is also antibacterial and is a good anti-oxidant, astringent, and soothes inflamed and irritated wounds and skin. Linden leaf is both a demulcent and astringent, making it an effective remedy for excessive dryness. The demulcent qualities add moisture to the body, while the astringent qualities tighten and tone tissues, helping to keep the moisture in the skin. St. Johns wort has antibacterial, antioxidant, and antiviral properties. Because of its anti-inflammatory properties, it has been applied to the skin to help heal wounds and burns. St. Johns Wort is very effective in relieving sore muscles and therefore sore feet, muscle strain, and tension. Garlic possesses antiviral characteristics as well as being an effective antifungal agent. Garlic contains diallyl sulphide (DAS) and diallyl disulphide (DADS0, which significantly inhibit proteinase, phospholipase secretion, and dimorphism in *Candida albicans*. These compounds can, therefore, act as a potent anti-fungal in the management of candidiasis. The botanical agents can be present in the therapeutic composition in an amount of between about 0.05 to 5% w/w of the composition. In certain embodiments, the botanical agent or agents are present in an amount of between about 0.025-0.30% w/w.

In one embodiment, the therapeutic composition can include an effective amount of cannabidiol (CBD) oil. CBD oil, the non-intoxicating marijuana extract, possesses antifungal, antibacterial, antiviral, and anesthetic properties. Advantageously, CBD oil is present in an amount between about 1-20% w/w of the formulation. In a preferred embodiment, the amount of CBD oil is between about 5-10% w/w of the composition. In a particularly preferred embodiment, the CBD oil is about 10% w/w of the formulation. In another aspect, CBD oil is replaced with an effective amount of ginger root oil, clove bud oil, or combinations thereof.

In some embodiments, the system or kit can further include a separate container comprising a hydrating composition as described below. Thus, it is contemplated that the system/kit can include both a container comprising the medicated pads as well as a separate container comprising a hydrating composition for applying to the affected area after the application of the medicated pad to a nail surface. The kit includes instructions for first cleaning the infected nail surface with a medicated pad as described above and then moisturizing the surrounding tissue with a hydrating composition to prevent the area from becoming dry, improving permeability, and promoting penetration of the epidermis by the active ingredients of the medicated pad. Optionally, the instructions can further include directions to massage the hydrating composition into the skin to reduce stiffness and fatigue, promote circulation, and hasten the absorption of therapeutic composition and/or hydrating composition.

The medicated cleansing pads prepares the affected surface, removes microbes and dead skin, treats the underlying infection, and lowers the pH of the skin surface to enhance the permeability of the skin and nails to a separate hydrating composition such as the Balm Riche All Natural Foot Cream™ moisturizer or Balm Riche All Natural Diabetic Foot Cream™ moisturizer (Dr. Rehm Remedies, San Marcos, Calif.). Advantageously, a suitable hydrating composition can includes, without limitation, water, aloe vera, xanthan gum, allantoin, sodium borate, lactic acid, vitamin C/ascorbic acid, tocopherol, a preservative such as phenoxyethenol, caprylyl glycol, potassium sorbate and/or hexylene glycol, Vitamin B3, Vitamin A, Vitamin D, shea butter, coconut oil, high oleic safflower oil, emu oil, glyceryl stearate, cetaryl alcohol, stearic acid, beeswax, granulated lecithin, tea tree oil, lavender oil, and botanicals such as chamomile, fever few, arnica, marigold, lime tree, St. Johns Wort and combinations thereof. Exemplary percentages of the effective amounts of the various hydrating components can be found in Table 1.

TABLE 1

Balm Riche Formula

| Ingredient/Common Name | INCI | Percentage (% w/w) |
|---|---|---|
| Water | Water | 35-55 |
| Aloe Vera Powder | Aloe barbadensis leaf | 0.05-1.0 |
| Xantham Gum | Xantham Gum | 0.05-1.5 |
| Allantoin | Allantoin | 0.05-5.0 |
| Borax | Sodium Borate | .25-2.0 |
| Lactic Acid | Lactic Acid | 0.2-2.0 |
| Citric Acid | Ascorbic Acid | .05-1.0 |
| Vitamin E Mixed Tocopherols | Tocopherol | 0.05-0.5 |
| Cap 5 Preservatives | Phenoxyethanol, caprylyl glycol, potassium sorbate, hexylene glycol | 0.05-2.0 |
| Vitamin B3 | Niacinimide | 0.01-1.0 |
| Vitamin A | Retinyl palmitate | 0.05-0.5 |
| Vitamin D | Cholecalciferol | 0.05-0.5 |
| Shea Butter | Butyrospermum parkii | 1-5 |
| Coconut Oil | Cocos nucifera | 1-10 |
| High oleic safflower oil | Carthamus tinctorius | 1-15 |
| Emu oil | Emu oil | 1-5 |
| Glyceryl stearate | Glyceryl stearate | 1-5 |
| Cetearyl alcohol | Ceteryl alcohol | 0.5-5 |
| Stearic acid | Stearic acid | 0.5-5 |
| Beeswax | Cera alba | 0.25-10.0 |
| Lecithin granules | Lecithin | 0.05-1.0 |
| Tea Tree Oil | Malaleuca alternifolia | 0.25-25.0 |
| Lavendar Oil | Lavandula angustifolia | 0.25-5.0 |
| Chamomile | Matricaria recutita flower | 0.10-5.0 |
| Fever few | Chrysanthemum parthenium oil | 0.10-5.0 |
| Arnica | Arnica montana | 0.10-5.0 |
| Marigold | Helianthus anuus, calendula officinalis | 0.10-5.0 |
| Lime tree | Citrus aurantifolio oil | 0.10-5.0 |
| CBD oil | Canabis sativa | 5.0-10% |
| St. Johns Wort | Hypericum perforatum | 0.10-5.0 |

A method of treating a nail infection is also provided. The method includes providing a medicated pad such as a pad treated with a therapeutic composition as described herein and cleaning the nailbed and surrounding tissue. One or more pads can be used to remove hard dead skin from the surface of the affected nail and surrounding tissue as well as to clean the surface of the nail bed while providing an antimicrobial treatment. As described above, the medicated pad is soaked, saturated, or otherwise treated with a therapeutic composition comprising an effective nail infection treatment amount of: an antifungal agent such as tolnaftate, botanicals selected from the group consisting of: chamomile, calendula, coneflower, linden leaf, oregano, garlic, St. Johns Wort, tea tree oil, lavender oil and combinations thereof; a disinfectant such as isopropyl alcohol; allantoin, urea, citric acid, optiphen, and combinations thereof. The disinfectant can include a fatty or wax alcohol such as lauryl, cetearyl, stearyl, and cetyl alcohol. In other embodiments, the disinfectant may be one of various glycols or isopropanol. Other disinfectants may include, without limitation, an effective amount of ethanol, ethyl alcohol, denatured alcohol, methanol, isopropyl alcohol, SD alcohol, benzyl alcohol, or combinations thereof. The pad removes debris and dead skin and the therapeutic composition treats the underlying infection, lowering the pH of the treatment surface, reducing inflammation, and increasing permeability of anti-infective agents such as an antifungal agent to expedite resolution of the infection. In use, the medicated pad serves to debride the surface of the nail and surrounding skin to remove fungal contaminates, the therapeutic composition penetrates the surface of the treated area to hasten absorption of the therapeutic agent and reduce microbial populations; and the cream serves to soften the treated area. The softening of the nail and surrounding tissue facilitates debridement as well as providing a more pliant nail. Some of the hallmarks of fungal nail infections is the yellowing and extreme hardening of the nail. Successful resolution of nail infections often requires that the infected/contaminated nail be trimmed to remove the yellowed areas attendant to infection. However, with hardened nails, it can be quite difficult to accomplish this trimming. By applying a cream such as the one detailed above as an adjuvant to the medicated pads with a therapeutic composition, the user is able to treat symptoms of the underlying infection, clean the nail surface, and soften the skin and nails to enable more effective trimming and debridement.

Optionally, the method of treatment further includes applying a hydrating composition to the affected nail surface and surrounding tissue after treatment with a medicated pad. The moisturizing agent prevents dryness around the nail surface as well as the surrounding tissue and promotes healing. The moisturizer can include, without limitation, one or more of the following components: glycerin, ceramides, urea, glycolic acid, hyaluronic acid, lactic acid, occlusive such as dimethicone, petrolatum, paraffin, and lanolin or combinations thereof, humectants, emollients, as well as natural botanicals such as aloe vera, chamomile, fever few, arnica, marigold lime tree, and St. John's Wort and combinations thereof, and essential oils such as tea tree oil, lavender oil, and combinations thereof. In one embodiment, the moisturizing agent is Balm Riche All Natural Foot Cream™ moisturizer or Balm Riche All Natural Diabetic Foot Cream™ moisturizer (Dr. Rehm Remedies, San Marcos, Calif.).

A system for reducing the symptoms skin conditions associated with the feet and hands is likewise contemplated. More particularly, skin conditions contemplated for treatment with the above-described medicated pad include any condition for which debridement and moisturizing of the affected area ameliorate symptoms of the condition. Exemplary conditions contemplated include, without limitation psoriasis, fungal infections such as ringworm and athlete's foot, eczema, and eczematous dermatitis. The condition can further include a bacterial infection, a viral infection, inflammation, pain, and combinations thereof.

Example 1

The efficacy of the disclosed kit for ameliorating signs of fungal contaminants and infections of the toe nails was studied. An individual presenting with dry skin and infected nail beds was identified. A photograph of the individual's untreated feet is set forth in FIG. 1. Notably, the individual's nails are discolored. The cuticles on the untreated toes are thick and in need of debridement. The surface of at least the left big toe had noticeable ridges and the surrounding tissue was dry and crusty.

Figure 2:
FIG. 2 is a color photograph of the individual's feet from FIG. 1 after being treated for 28 days with the disclosed composition and kit.

The individual treated the surface of the nails and surrounding tissue with medicated pads moistened with a therapeutic solution as described above. The textured medicated pad was used to scrub the surface of the nails and surrounding tissue and reduce the amount of dead skin and fungal contaminants. After 28 days, a second photograph was taken as illustrated in FIG. 2. Notice that the signs and symptoms of fungal infection on the toenails have been dramatically reduced. The nail beds are clean and no longer discolored. The surrounding skin is likewise clean and moisturized. The cuticles and nails have been softened.

In other aspect, disclosed herein is a nail bandage to offer the end user a convenient, state of the art method of treating their nail fungus and at the same time debride, soften and condition the healthy part of the nail plate, nail bed and surrounding skin. Also, treatment with a bandage configured to be worn on the effected nail also offers some protection against the reoccurrence of fungus infection of the nail and surrounding nail structures.

Applying a bandage treated with an effective amount of a therapeutic composition as disclosed herein at least once a day to fight fungus infection of the nails provide a convenient, healthier and less costly way of dealing with nail fungus infection, especially for those individuals that are more likely to be afflicted with this condition.

Fungal nail infection is extremely common with 20 percent of the general population affected, but age is an important factor here. Half of the sufferers are people older than 70 and 75 percent of people over 60-years-old affected. Other risk factors include diabetes, vascular insufficiency, or malnutrition. Often, the problem is cosmetic, but many patients also experience pain. Sometimes toenail fungus can lead to more serious infections, especially in those that have chronic diseases.

Psychological and/or social issues are commonly part of the clinical picture associated with fungal infections of the nails. In addition, besides the simplicity of applying a bandage treated with compositions described herein, a pre-treated bandage has additional benefits including cost factors associated with prescription and oral medications can be prohibitive, especially for those who are on fixed incomes or treating chronic diseases and their comorbidities. Often insurance coverage and out of pocket costs are cost-prohibitive to those with highest likelihood of contracting onychomycosis. A pre-treated bandage as a delivery of the compositions disclosed herein alleviates these concerns.

Onychomycosis is caused by fungi such as dermatophytes, non-dermatophyte molds and yeasts (mainly *Candida* species). Of these 80% of the nail infections are caused by dermatophytes (*Trichophyton rubrum*). This fungus is an infection of the nail plate and often involves the surrounding tissues, often referred to the nail apparatus. Pathogens can colonize and/or infect various parts of the various parts of this nail apparatus.

The nail apparatus is composed of the following elements:

1. The Nail Plate

The nail plate (corpus unguis) is the hard, translucent portion of the nail, made of translucent keratin protein. Several layers of dead, compacted cells cause the nail plate to be strong but flexible. In addition to the mineral content of the nail, human nail plates also have a three-layered protein structure which includes alpha keratin, keratin associated proteins and keratin microfibrils which is found in the globular matrix 2. The Nail Matrix This is the nail root which is the growing part, under the skin at the proximal end of the nail plate.

3. The Nail Bed

This is composed of adherent connective tissue that underlies the nail plate

4. The Lunula

This is the crescent shaped whitish area of the nail bed

5. The Eponychium or Cuticle

This is the fold of the skin at the proximal end of the skin

6. The Paronychium

This refers to the fold of the skin on the sides of the nail.

7. The Hyponychium

The hyponychium refers to the attachments between the skin of the finger or toe and the distal end of the nail.

Onychomycosis is classified clinically as:

1. Distal and Lateral Subungual Onychomycosis (DLSO)

It affects the hyponychium, often at the lateral edges initially, and spreads proximally along the nail bed resulting in subungual hyperkeratosis and onycholysis although the nail plate is not initially affected. Distal and lateral subungual onychomycosis may be confined to one side of the nail or spread sideways to involve the whole of the nail bed, and progresses relentlessly until it reaches the posterior nail fold.

2. Superficial White Onychomycosis (SWO)

Superficial white onychomycosis is also a dermatophyte infection, which is caused by *T. mentagrophytes*. It is much less common than distal and lateral subungual onychomycosis and affects the surface of the nail plate rather than the nail bed. Discoloration is white rather than cream and the surface of the nail plate is noticeably flaky.

3. Proximal Subungual Onychomycosis (PSO)

Proximal subungual onychomycosis is an uncommon type of fungal nail infection in which invasion begins from the undersurface of the proximal nail fold and then progresses distally.

The fungus initially invades the stratum corneum of the proximal nail fold and subsequently penetrates the newly formed nail plate. The nail changes are either diffuse patches or transverse striate patterns, both present clinically as a white discoloration under the proximal nail plate in the area of the lunula; the distal nail unit usually remaining normal. As opposed to SWO, the nail plate is intact. Subungual hyperkeratosis, onychomadesis, and eventual destruction and shedding of the entire nail plate may occur in advanced disease. Because it is so infrequent, some authors believe that a preceding episode of trauma is a prerequisite for it to occur in Immunocompetent patients.

4. Candidial Onychomycosis

Infection of the nail with *Candida* yeasts may present in one of the following four ways, (i) chronic paronychia with secondary nail dystrophy; (ii) distal nail infection; (iii) chronic mucocutaneous candidiasis; and (iv) secondary candidiasis. Chronic paronychia of the nails generally occurs in patients with wet occupations. Swelling of the posterior nail fold occurs secondary to chronic immersion in water or possibly due to allergic reactions to some foods, and the cuticle becomes detached from the nail plate thus losing its water-tight properties. Microorganisms, both yeasts and bacteria, enter the subcuticular space causing further swelling of the posterior nail fold. Distal nail infection with *Candida* yeasts is uncommon and virtually all patients have Raynaud's phenomenon or some other form of vascular insufficiency.

Chronic mucocutaneous candidiasis, involves the mucous membranes which is caused due to diminished cell-mediated immunity. This involves a direct invasion of the nail plate and may affect the entire thickness of the nail plate potentially involving severe deformity of the proximal and lateral nail folds. Secondary candidal onychomycosis occurs due to other diseases of the nail, mostly psoriasis. *Candida* onycholysis can occur when the nail plate has separated from the nail bed. It can start with a distal subungual hyperkeratosis which lifts the nail plate off of the nail bed.

5. Total Dystrophic Onychomycosis

Total dystrophic onychomycosis is used to describe end-stage nail disease and is considered to be the end result of any of the four main patterns of onychomycosis where the entire nail becomes thick and dystrophic.

A fungal nail infection occurs from the overgrowth of fungi in, under, on or around the nail plate. It is obvious then that all portions of the nail apparatus can be involved and treatment has to involve all of the tissues.

As will be appreciated by a skilled artisan, to adequately treat a fungus infection of the nail apparatus, it is important that the nail plate be penetrated and debrided of substantially all pathogenic material and the surround skin and other tissues be treated and conditioned to optimize the integrity and immune potential of these areas. The disclosed bandage is designed to do just this. It offers penetration of the effective treatment factors into the nail plate and in effect also debriding it, breaking it down and then allowing further treatment and conditioning of the surround skin and tissues in, under, on and around the nail plate.

By offering a compressed contact with the treatment elements and the nail apparatus for the designated period of time, optimal resolution of the mycosis is more likely to occur with a bandage treated with the disclosed compositions.

Therefore, an adequate anti-onychomycotic system may involve the following:
1. Penetration of the Nail Plate
2. Auto-debriding of the pathogenic elements
3. Antifungal therapy
4. Conditioning the skin areas that surround the nail plate and assist in preventing reoccurrence.

The disclosed nail bandage offers persons who have a of high risk for onychomycosis, and those with immune deficiencies, an easy, palatable affordable way to treat and prevent fungus infection of the nails. From a public health point of view, billions of dollars a year are spent on nail related problems. The disclosed nail bandage offers significant recourse to a myriad of problems associated with the unchecked, widespread and very costly pandemic associated with onychomycosis.

The design the nail bandage fits a nail bed. In an embodiment, the nail bandage is sized to fit a toe. Advantageously, the nail bandage is constructed so as to not slip off and the contact therapy pad provides a therapeutic composition as described herein. The therapy pad can be pre-treated with the therapeutic composition such that the nail bandage is manufactured with the therapeutic composition instilled on the therapy pad prior to market. In another embodiment, the bandage can be provided as part of a kit comprising the therapeutic composition and the user can administer the therapeutic composition onto the therapy pad. In one embodiment, the therapy pad is pre-instilled/pretreated or can be instilled by the consumer with the nail treatment ingredients aftermarket such that the nail treatment ingredients are positioned over a nail bed and released for at least one day for optimal results. It will be appreciated that the nail bandage can be applied for longer than one day or for less time than one day:

The nail bandage is designed to deliver treatment to the direct nail apparatus over a 24-hour period while covering the area, protecting it from pressure from foot wear and other forces of walking as well as allowing the user to have a therapeutic bandage on their toe while being able to use their normal shoes and socks.

Figure 3:
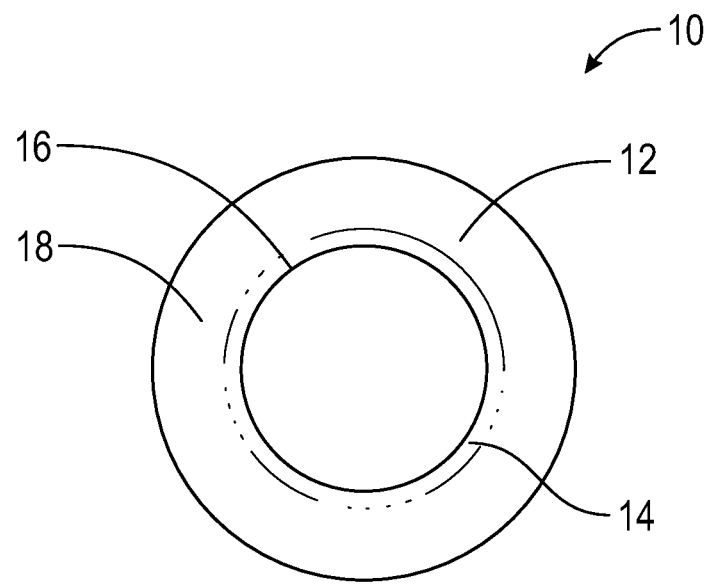
FIG. 3 is a photograph of the top side of a nail bandage as described herein.
Figure 4:
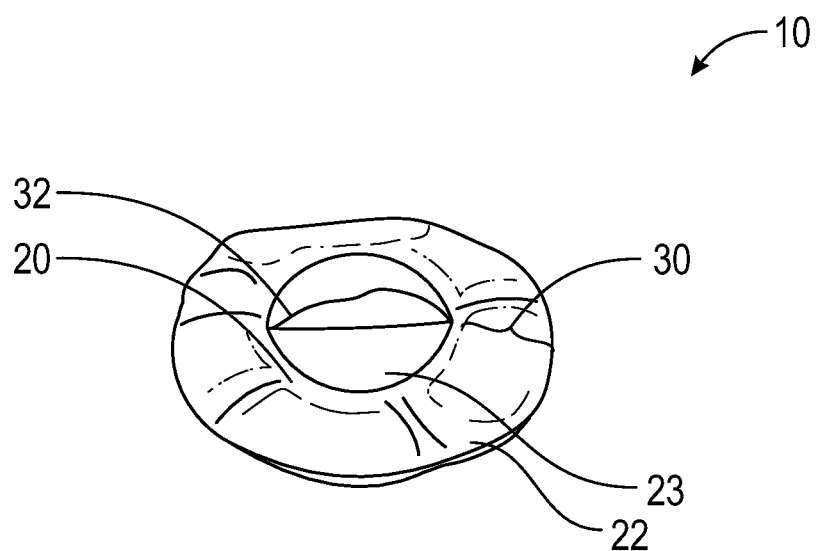
FIG. 4 is a photograph of the skin attachment side of an embodiment of a nail bandage as described herein, including an attachment of an inner reservoir material.
Figure 5:
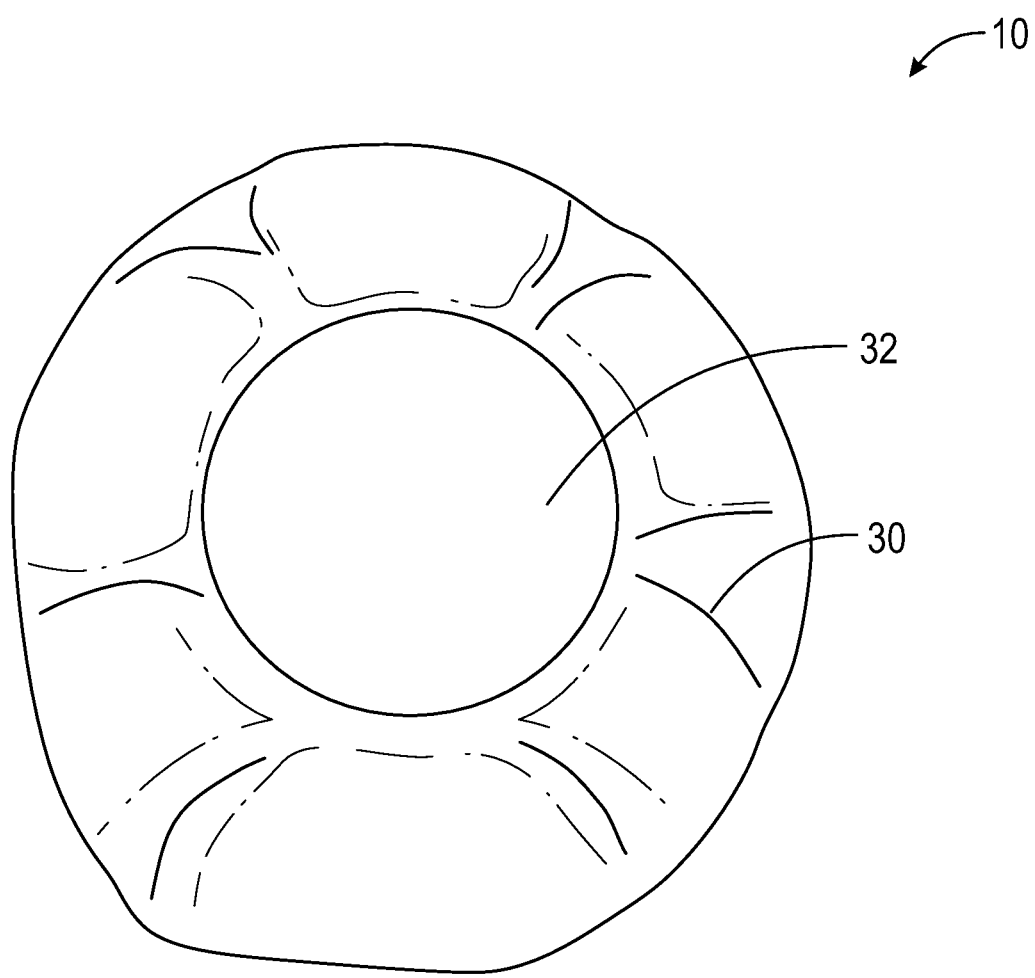
FIG. 5 is a photograph of the skin attachment side of an embodiment of a nail bandage having a therapeutic pad centered therein.

In one embodiment, a nail bandage comprising a pre-treated anti-fungal therapy pad for treating onchomycosis is provided. The anti-onchomycotic system is comprises a nail bandage 10 having a bandage body 12. The bandage body 12 includes an upper surface (the surface that faces away from the skin surface) 26 and a lower surface (skin contacting surface) 24, at least one protective release tab (not illustrated) removably disposed on the lower surface, and an absorbent, nail-contacting anti-fungal therapy pad. Referring to FIGS. 3-5, a first embodiment of a bandage 10 for anti-onychomycosis is illustrated. The bandage 10 includes a bandage body 12. The bandage body 12 has the shape of an inverted saucer with a depression 14 defined by a sidewall 16 that has the shape of an annulus, preferably a continuous annulus. The sidewall 16 transitions to a compressed ring 18. The lower inside surface of the sidewall 16 defines an inner margin 20, while the outside edge of the compressed ring 18 defines an outer margin 22. The inner and outer margins are preferably, but not necessarily continuous and circular in shape. The bandage body 12 can be any conventional shape that can accommodate the geometries of the nail bed of a toe or finger. In a preferred embodiment, the bandage body is a substantially round or oval shaped enclosure. The bandage body 12 includes an upper surface (the surface that faces away from the skin surface) and a lower surface (skin contacting surface), at least one protective release tab (not illustrated) removably disposed on the lower surface, and an absorbent, nail-contacting anti-fungal therapy pad 32. Preferably, the anti-fungal therapy pad is positioned substantially central relative to the enclosure. At least a portion of the lower surface contacts a user's nail bed. Adhesive is at least partially disposed on the lower surface. The therapy pad 32 is disposed on the lower surface. One or more protective release tabs are removably disposed on the lower surface. The number of release tabs may be influenced by the shape of the bandage The skin-contacting surface 24 of the bandage 10 is best seen in FIGS. 4 and 5. The bandage 10 further includes a bandage body 12 having a sidewall 16 that forms a margin 20 defining an opening 28, and a skin-facing surface 30 surrounding the opening 28. The skin contacting surface 24 includes an adhesive material to removeably secure the bandage to the surface of a nail. Advantageously, the adhesive material is a ring of adhesive material and may further include a release liner on its lower surface which is stripped away when the bandage 10 is to be attached to the nail of a patient. The bandage 10 is attached to the skin of a patient by the adhesive material such that the sidewall 16 and the inner margin 20 define an opening 23 that surrounds the nail. Above the opening 23, the space in the depression 14 forms a recess over the nail to house a therapy pad 32, disposed in the opening of the bandage body 12. The bandage body 12, the sidewall 16, and the compressed ring 18 are formed integrally. Preferably, the integral structure is formed of a material that is light, flexible, yet of a nature that provides structural integrity to the bandage 10. As an example, the bandage 10 may be formed by molding open cell foam material such as polyurethane. The material is compressed to form the compressed ring 18 only for the purpose of profiling the bandage 10. Such profiling is not a necessary element of the invention.

The bandage body can be constructed from any conventional biocompatible materials. In one embodiment, the bandage body is constructed from silicone. Alternatively, the bandage body is constructed from fabric, plastic, and/or silicone. The therapy pad is constructed of a nonwoven material made from suitable fibers such as cotton, rayon, polyester, polyolefin, or combinations thereof. The protective release tab may be made from paper with a silicone release material coated thereon and/or may be constructed of a low surface energy plastic film such as polyethylene or polystyrene which, optionally, can have a silicone release material or the like applied thereto. The release coated surface of protective release tabs is configured to contact adhesive and the release coating on protective release tabs are such that when those tabs are removed, adhesive is exposed prior to application of the bandage to the skin. Adhesive is made from any conventional skin compatible material. In a preferred embodiment, the adhesive is free or substantially free of latex. The adhesive bandage can be individually packaged between two sheets of paper which are sealed cohesively about the edges.

A therapy pad contains or is capable of being instilled with a therapeutic composition as described herein to treat fungal infections of the nail as well as to condition the nail bed. The bandage with the therapy pad are size shaped to various sizes appropriate for the nail areas that would come in contact with the nail apparatus area. The therapy pad can be adhered to the skin-facing surface of the bandage via medical grade tape or glue. In one embodiment, the therapy pad is not integral to the bandage structure but rather is a separate structure that can be positioned over the recess in the bandage by the user. As detailed above, the therapy pad can be pre-treated with an anti-fungal therapeutic agent or the user can wet or otherwise dose the therapy pad with the anti-fungal therapeutic separately after market. The therapy pad can be integrated into the bandage, separately positionable, or it can be affixed to a medical grade tape to securely attach the bandage and therapy pad to the skin.

In a particularly preferred embodiment, an effective amount of spider web is introduced to the therapy pad. Spider web strands promote healing. Spider web or cobweb includes proteinaceous silk extruded from the spinnerets gland of a spider. Rich in vitamin K, the spider web strands hasten healing and promote healing from fungal infections of the nail bed. Insoluble in aqueous, the spider web can be suspended in an ointment. Spider web strands can reinforce the therapeutic pad and provide additional effectiveness for the treatment of fungal infections to the nails. Additionally, the use of tape to enhance circulation through nano technology is specifically contemplated to improve the absorption of the therapeutic elements.

Example 2

The therapeutic material infiltrated into the bandage include.
a. Urea as the penetrating material
b. Tolnaftate or anti-fungal medication
c. essentials oils/cbd/aloe/clove/cinnamon/tea tree etc This, therefore, provides an adequate anti-onychomycotic system that involves the following:
1. Penetration of the Nail Plate
2. Auto-debriding of the pathogenic elements
3. Antifungal therapy
4. Conditioning the skin areas that surround the nail plate and assist in preventing reoccurrence.

The bandage with therapeutic pad is positioned and adhered to a nail bed. The bandage is secured to the nail bed for a period of about 24 hours. After 24 hours, the bandage is replaced by another bandage and the process is repeated. Over a period of time, a reduction in fungal infection is observed on the nail treated with the bandage.

The above description of disclosed embodiments is provided to enable any person skilled in the art to make or use the invention. Various modifications to the embodiments will be readily apparent to those skilled in the art; the generic principles defined herein can be applied to other embodiments without departing from spirit or scope of the invention. Thus, the invention is not intended to be limited to the embodiments shown herein but is to be accorded the widest scope consistent with the principles and novel features disclosed herein.

What is claimed is:

1. A method of treating a nail infection, comprising:
providing a bandage comprising a medicated pad, wherein the medicated pad is instilled with a therapeutic solution comprising:
an effective amount of an anti-fungal agent,
an effective amount of a moisturizing agent, and
an effective amount of a botanical agent; and
providing a hydrating composition prior to applying said bandage,
wherein the hydrating composition comprises:
an effective amount of shea butter;
an effective amount of aloe vera powder;
an effective amount of *arnica;*
an effective amount of vitamins selected from the group consisting of vitamin C, vitamin A, vitamin E, vitamin B3, vitamin D, and combinations thereof;
an effective amount of emu oil; and
an effective amount of urea; and
applying the hydrating agent to the surface of the nail and the surrounding tissue to clean the surface of the nail and the surrounding tissue; and
applying the bandage to the surface of a nail and surrounding tissue.

2. The method of claim 1 wherein the antifungal agent is tolnaftate.

3. The method of claim 1, wherein the moisturizer is selected from the group consisting of allantoin, urea, and combinations thereof.

4. The method of claim 1, wherein the botanical agent is selected from the group consisting of extract of calendula, chamomile, cornflower, linden leaf, St. Johns Wort, garlic, oregano oil, tea tree oil, lavender oil, clove oil, cinnamon oil, CBD oil, and combinations thereof.

5. The method of claim 1, wherein the therapy pad is instilled with an effective amount of a disinfectant.

6. The method of claim 5, wherein the disinfectant is isopropyl alcohol.

7. The method of claim 1, wherein applying the hydrating agent comprises massaging the hydrating agent into the nail bed and surrounding skin surfaces.

* * * * *